United States Patent [19]
Brakier-Gingras et al.

[11] Patent Number: 5,707,866
[45] Date of Patent: Jan. 13, 1998

[54] DNA OLIGOMERS FOR INHIBITION OF HIV BY DECREASING RIBOSOMAL FRAMESHIFTING

[75] Inventors: Léa Brakier-Gingras, Outremont; Pierre Melançon, Montréal; Marc Côté, Montréal; Catherine Payant, Montréal, all of Canada

[73] Assignee: Universite de Montreal, Montreal, Canada

[21] Appl. No.: 651,835

[22] Filed: May 21, 1996

Related U.S. Application Data

[63] Continuation-in-part of Ser. No. 409,852, Mar. 23, 1995, abandoned, which is a continuation-in-part of Ser. No. 220,604, Mar. 30, 1994, abandoned.

[51] Int. Cl.$^6$ .............. C12N 15/85; C12Q 1/68; C07H 21/04
[52] U.S. Cl. ............ 435/367; 435/6; 435/172.3; 435/320.1; 435/366; 536/23.1; 536/24.5
[58] Field of Search .............. 536/24.5, 23.1; 514/44; 435/6, 172.3, 320.1, 366, 367

[56] References Cited

FOREIGN PATENT DOCUMENTS

| | | |
|---|---|---|
| 89/06704 | 7/1989 | WIPO. |
| WO90/08841 | 8/1990 | WIPO. |

OTHER PUBLICATIONS

Gura, T. (1995) Science 270:575–7.
Pinard et al. (1994) Nuc. Acids Res. 22:619–24.
Gutell, R.R. (1993) Nuc. Acids Res. 21:3051–4.
Hogrefe et al. (1993) Nuc. Acids Res. 21:2031–8.
Mader et al. (1993) Proc. Natl. Acad. Sci. USA 90:5603–7.
Milligan et al. (1993) J. Med. Chem. 36:1923–37.
Neefs et al. (1993) Nuc. Acids Res. 21:3025–49.
Pinard et al. (1993) FASEB J. 7:173–6.
Stein et al. (1993) Science 261:1004–12.
Amann et al. (1992) Appl. Env. Microbiol. 58:614–23.
Crooke et al. (1992) Ann. Rev. Toxicol. 32:329–76.
Hatfield et al. (1992) Adv. Virus Res. 41:193–239.
Vickers et al. (1992) Nuc. Acids Res. 20:3945–53.
Noller, H.F. (1991) Ann. Rev. Biochem. 60:191–227.
Park et al. (1991) J. Virol. 65:5111–7.
Jacks, T. (1990) Curr. Top. Microbiol. Immunol. 157:93–124.
Gravel et al. (1989) Nuc. Acids Res. 17:2723–32.
Sambrook et al. (1989) Molecular Cloning: A laboratory Manual, 2nd Ed., Cold Spring Harbor Lab., Cold Spring Harbor, New York.
Terwilliger et al. (1989) Proc. Natl. Acad. Sci. USA 86:5163–7.
Chesebro et al. (1988) J. Virol. 62:3779–88.
Rairkar et al. (1988) Nuc. Acids Res. 16:3113.
Raue et al. (1988) Prog. Biophys. Mol. Biol. 51:77–129.
Lee et al. (1987) J. Clin. Microbiol. 25:1717–21.
Gonzalez et al. (1986) Am. J. Hum. Genet. 38:419–27.
Melancon et al. (1984) Biochem. 23:6697–703.
Miller, J.H. (1972) Experiments in Molecular Genetics, Cold Spring Harbor Laboratory Press, New York, pp. 352–355.
Anazodo et al. (1995) J. Virol. 69:1794–801.
Gewirtz et al. (1996) Proc. Natl. Acad. Sci. USA 93:3161–3.
Matteucci et al. (1996) Nature 384 (Supp.7):20–2.
Weiss, Science News, 139:108–109, 1991.
Wagner, Nature, 372:333–335, 1994.
Stull et al., Pharmaceutical Research, 12(4):465–483, 1995.
Wu–Pong, Pharmaceutical Technology, 18:102–114, 1994.
Miller et al., Parasitology Today, 10(3):92–97, 1994.
Rojanasakul, Advanced Drug Delivery Reviews, 18:115–131, 1996.

*Primary Examiner*—John L. LeGuyader
*Attorney, Agent, or Firm*—Klauber & Jackson

[57] ABSTRACT

The invention relates to the use of antisense DNA oligomers to decrease the occurrence of ribosomal frameshifting required for the production of HIV enzymatic proteins when translating HIV messenger RNA, which should interfere with the production of virions and disrupt HIV life cycle. The antisense DNA oligomers are complementary to regions of the RNA of the small ribosomal subunit of mammalian cells, which are involved in the control of translation fidelity.

5 Claims, 3 Drawing Sheets

FIG. 1

```
5'  GGTCGACAGGCTAATTTTTTAGGGAAGATCTGGCCTTCCTACAAGGGAAGGCCAGGGACATG  3'
    GTACCCAGCTGTCCGATTAAAAAATCCCTTCTAGACCGGAAGGATGTTCCCTTCCGGTCCCT
3'                                                                5'
```

FIG. 2A

```
5'  GGTCGACAGGCTAATTTTTTAGGGAAGATCTGGCCTTCCTACAAGGGAAGGCCAGGGACATG  3'
    GTACCCAGCTGTCCGATTAAAAAATCCCTTCTAGACCGGAAGGATGTTCCCTTCCGGTCCCT
3'                                                                5'
```

FIG. 2B

```
5'
ATG GGT CGA CAG GCT AAT TTT TTA GGG AAG AAT CTG GCC TTC CTA CAA GGG AAG GCC AGG GAC ATG CAG AAA AAA ATC   arg glu asp leu ala phe leu gln gly lys ala arg asp met gln lys lys ile
met gly arg gln ala asn phe leu                                                                                                                     CAT enzyme      3'
```

FIG. 3A

```
5'
ATG GGT CGA CAG GCT AAT TTT TTA GGG AAG AAT CTG GCC TTC CTA CAA GGG AAG GCC AGG GAC ATG CAG AAA AAA ATC
met gly arg gln ala asn phe leu gly lys asn leu ala phe leu gln gly lys ala arg asp met gln lys lys ile
                                                                                                    CAT enzyme      3'
```

DNA OLIGOMERS FOR INHIBITION OF HIV BY DECREASING RIBOSOMAL FRAMESHIFTING

RELATED APPLICATION

This application is a continuation-in-part of application Ser. No. 08/409,852 filed on Mar. 23, 1995, now abandoned, which is a continuation-in-part of application Ser. No. 08/220,604 filed Mar. 30, 1994, now abandoned.

BACKGROUND OF THE INVENTION (a) Field of the Invention

The invention relates to the use of antisense DNA oligomers to decrease the occurrence of ribosomal frameshifting required for the production of HIV enzymatic proteins when translating HIV messenger RNA, which should interfere with the production of virions and disrupt HIV life cycle.

(b) Description of Prior Art

Information contained in a messenger RNA is translated into proteins by ribosomes in sequential non-overlapping triplets, from a starting point referred to as the initiation site. Errors in translation of a messenger RNA may occur through misreading of the triplets or shift of the reading frame, generating faulty proteins.

Retroviruses carry their genetic code in the form of RNA and utilizes an enzyme called reverse transcriptase to convert their genetic code or viral RNA into a proviral DNA that becomes integrated into the host cell DNA. These integrated proviruses are duplicated with normal cellular genes during each cell division. Thus, all the progeny of the originally infected cell will contain the retroviral DNA. In addition, multiple copies of the infectious virus may be produced. The production of these virions cause other cells to become infected.

Retroviruses cause both malignant and nonmalignant diseases. Expression of the viral genes of some retroviruses may be oncogenic, converting the cell into a cancer, or may have other pathologic effects that may alter normal cell function or produce cell death. The same virus may cause different diseases in different animals. Of the retroviruses known to infect humans, HTLV types I and II are associated with lymphoid neoplasms and neurologic diseases but not with severe immunosuppression, while human immunodeficiency virus (HIV) causes immunosuppression but does not appear to cause neoplasms directly. HIV is one of the retroviruses of interest in accordance with the present invention.

The pol gene of all retroviruses codes for enzymatic activities essential for reverse transcription, proviral integration and protease activity that mediates cleavage of viral precursor proteins. Interestingly, in human immunodeficiency virus (HIV-1), the viral pol gene is expressed via a ribosomal frameshift when ribosomes translate the unspliced HIV mRNA species (reviewed in Jacks, T. (1990) *Curr. Top. Microbiol. Immunol.*, 157, 93–124; Hatfield et al. (1992) *Adv. Virus Res.*, 41, 193–239). The efficiency of this frameshift determines the ratio of the gag gene product, a viral core protein, and the pol gene products. Changes in that ratio may affect dramatically virus assembly (Park, J. and Morrow, C. D. (1991) *J. Virology*, 65, 5111–5117).

Vickers and Ecker ((1992) *Nucleic Acids Research*, 20, 3945–3953) showed that the use of oligonucleotides targeted to the gag-pol frameshifting region in HIV messenger RNA causes an increase in the occurrence of ribosomal frameshifting. These oligonucleotides are specific to the HIV gag-pol region, and hence, are affected by mutations which might alter the viral messenger RNA sequence.

It would be highly desirable to be provided with means to decrease ribosomal frameshifting occurring in mammalian cells which would affect vital expression of retrovirus without causing side effects to the cells.

SUMMARY OF THE INVENTION

One aim of the present invention is to provide antisense DNA oligomers to decrease the occurrence of ribosomal frameshifting in human cells which affects viral expression of retroviruses without causing side effects to the cells.

Another aim of the present invention is to provide such antisense DNA oligomers which are not affected by mutations in the viral messenger sequences.

The antisense DNA oligomers of the present invention offer the following advantages compared to those of Vickers and Ecker ((1992) *Nucleic Acids Research*, 20, 3945–3953).

a) They decrease the ribosomal frameshifting, which is more likely to affect dramatically the production of virions, by comparison with oligonucleotides that increase ribosomal frameshifting.

b) They are targeted to the ribosomes and not to HIV gag-pol region. Therefore, their efficiency is not affected by mutations which might alter the viral messenger RNA sequence. Furthermore, they have a larger spectrum of action, since they can be used against any type of retroviruses, which requires a ribosomal frameshifting for the production of virions.

In accordance with the present invention there is provided antisense DNA oligomers which are complementary to portions of regions of the RNA of the small ribosomal subunit of human cells, which are selected from the group consisting of:

a) nucleotides 595 to 641 in human 18S rRNA corresponding to region 530 in *E. coli* 16S rRNA; and b) nucleotides 1182 to 1220 in human 18S rRNA corresponding to region 900 in *E. coli* 16S rRNA;

whereby, said oligomers decrease the occurrence of ribosomal frameshifting and inhibit the expression of viral enzymatic proteins.

In accordance with the present invention the antisense DNA oligomers which have been used to define the two above-noted regions a) and b) are selected from the group consisting of:

TGCTGGCACGGAGTTAGCCGG, (SEQ ID NO:3)

GGCTGCTGGCACGGAGTTAGCCGG, (SEQ ID NO:4)

GCACCCTCCGTATTACC, (SEQ ID NO:5)

GCGGCTGCTGGC, (SEQ ID NO:6)

CGCGGCTGCTGG, (SEQ ID NO:7); and

CGTCAATTCCTTT, (SEQ ID NO:9).

In accordance with the present invention there is provided a method for the treatment of retrovirus infection in a host, which comprises administering to said host the antisense DNA oligomers of the present invention in association with a pharmaceutically acceptable carrier, whereby the expression of viral enzymatic proteins is inhibited.

In accordance with the present invention there is provided a pharmaceutical composition for the treatment of retrovirus infection in a host, which comprises antisense DNA oligomers of the present invention in an amount sufficient to substantially inhibit the expression of viral enzymatic proteins, and a pharmaceutically acceptable carrier.

For the purpose of the present invention the following terms are defined below.

"Retrovirus" refers to HIV, human T-cell leukemia virus type 1 (HTLV-1), and any human retroviruses requiring ribosomal frameshifting for expressing pol gene.

The term "sufficient amount" refers to the amount of antisense DNA oligomers of the present invention required to substantially inhibit enzymatic protein expression of the retrovirus. The precise effective amount will vary with the nature of antisense DNA oligomers used and may be determined by one of ordinary skill in the art with only routine experimentation.

DETAILED DESCRIPTION OF THE INVENTION

In accordance with the present invention, firstly, it is demonstrated that it is possible to influence the translational accuracy of ribosomes, using a simple assay: misreading of an artificial messenger poly(U), which codes for phenylalanine. Misreading is assessed by measuring the incorporation into the protein chain of leucine, a non-cognate amino acid. The agents used to modulate translational accuracy are oligodeoxyribonucleotides referred to as "antisense DNA oligomers", complementary to specific regions in the RNA of the small ribosomal subunit, which are involved in the control of translation fidelity.

In accordance with the present invention, secondly, it is demonstrated that antisense DNA oligomers complementary to specific regions of the RNA of the small ribosomal subunit can decrease ribosomal frameshifting. In this study, a natural mRNA coding for a reporter protein is used, the chloramphenicol acetyltransferase (CAT). The gene corresponding to this messenger has been modified, so that the beginning of the coding region contains the region where frameshift occurs in HIV mRNA, that is a shifty heptanucleotide followed by a stem/loop structure. Expression of CAT requires ribosomal frameshifting in that system.

1. Effect of antisense DNA oligomers on misreading of poly(U)

Poly(U) codes for the synthesis of polyphenylalanine. Misincorporation of leucine by ribosomes in a poly(U)-directed system indicates errors in translation. Among agents which influence leucine incorporation, potential candidates are found which might interfere with frameshifting when ribosomes translate HIV mRNA. Whether these agents decrease or increase misreading of poly(U) was not important per se at this stage of the work. What was important was to demonstrate that antisense oligomers can influence the control of translation accuracy.

Methods

Ribosomes and enzymes required for translation were isolated by standard procedures (Melancon, P. et al. (1984) *Biochemistry*, 23, 6697–6703) from *E. coli* strain K12A19 (obtained from *E. coli* Genetic Stock Center, Yale University, under accession number CGSC No. 5997). Desoxyribonucleotides complementary to specific regions of 16S rRNA were synthesized on a Pharmacia Automatic Synthesizer™ and purified by polyacrylamide gel electrophoresis. Poly(U)-directed misincorporation of leucine and incorporation of phenylalanine was adapted from standard procedures (Gravel, M. et al. (1989) *Nucleic Acids Research*, 17, 2723–2732). When measuring phenylalanine incorporation, the reaction mixture (100 μl) contained: 1 $A_{260}$ unit of 70S ribosomes (1 $A_{260}$ unit=24 pmol), 4 μg poly(U), 50 mM Hepes-KOH, pH 7.9, 60 mM $NH_4Cl$, 10 mM magnesium acetate, 16 mM 2-mercaptoethanol, 0.25 mM ATP, 0.25 mM GTP, 8 mM phosphoenolpyruvate, 0.3 μg pyruvate kinase, 75 μg *E. coli* stripped tRNA, an optimal amount (about 300 μg protein) of high-speed postribosomal supernatant (S150) and 10 μM [$^3$H]phenylalanine (5 Ci/mmol; 5 μCi). When measuring leucine misincorporation, the non-cognate amino acid, [$^3$H]leucine (5 Ci/mmol; 5 μCi), and the cognate amino acid, [$^{12}$C] phenylalanine, were added simultaneously at a concentration of 1 μM and 10 μM respectively.

When poly(U)-directed incorporation was performed in the presence of antisense DNA oligomers, these oligomers were added at a molar ratio of 30 per ribosome, before starting protein synthesis by addition of poly(U).

Results and discussion

Figure 1:
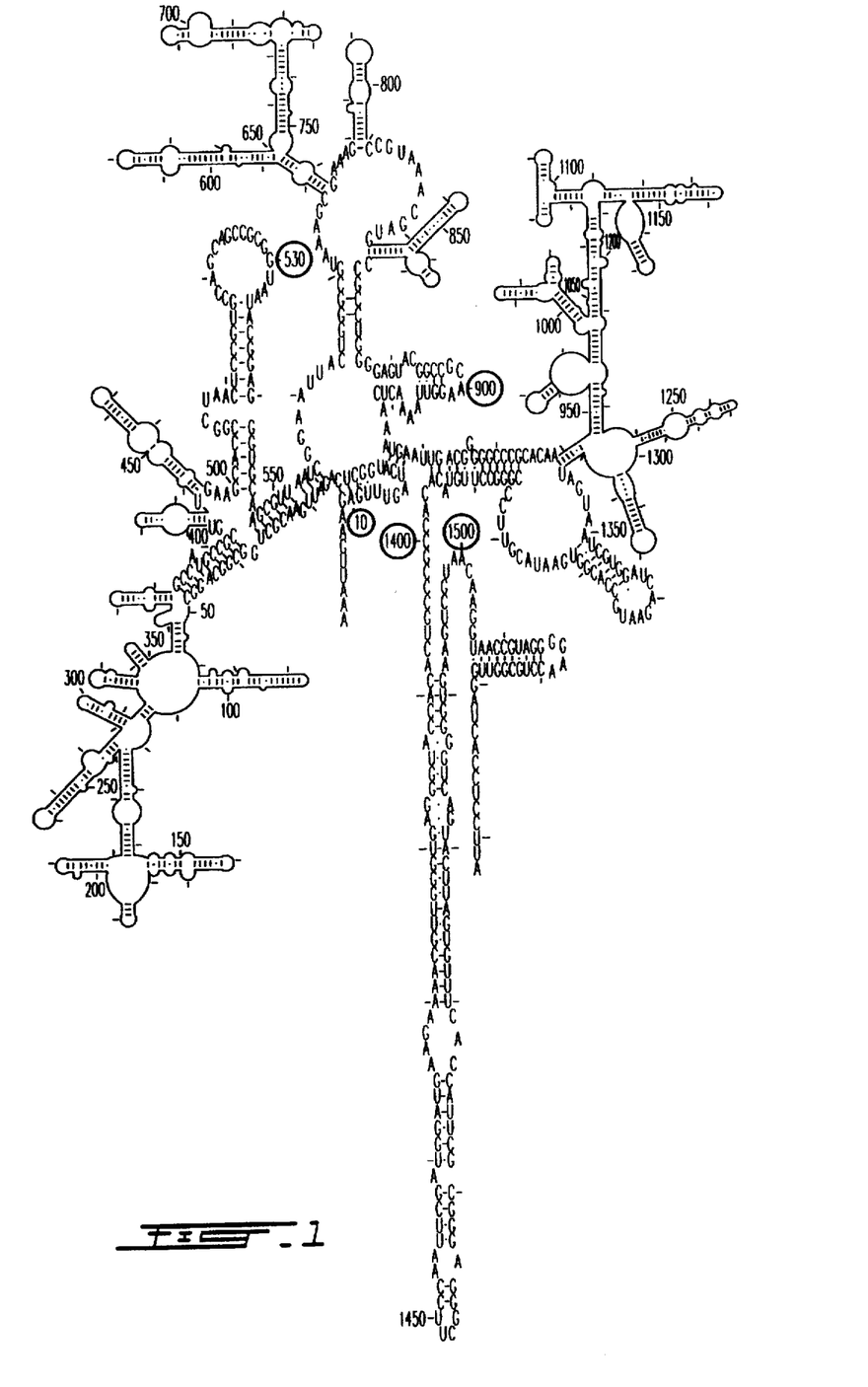
FIG. 1 illustrates the structure of E. coli 16S ribosomal RNA.

A survey of the literature (Noller, H. F. (1991) *Annu. Rev. Biochem.*, 60, 191–227), plus recent studies in our laboratory (Pinard, R. et al. (1993) FASEB J., 7, 173–175; Pinard, R. et al. (1994) *Nucleic Acids Research*, 22:619) have suggested that specific regions of the 16S ribosomal RNA in the small ribosomal subunit are important for the control of translational accuracy (FIG. 1). FIG. 1 illustrates the structure of *E. coli* 16S ribosomal RNA (Gutell, R. R. (1993) *Nucleic Acids Research*, 21, 3051–3057). Circles indicate the so-called regions 530 and 900 which are involved in the control of translational accuracy. Therefore, whether desoxyribonucleotides complementary to these regions could affect (whether decrease or increase) translational accuracy was investigated. Examples of antisense DNA oligomers which have been assayed are listed in Table 1 below.

TABLE 1

List of antisense DNA oligomers targeted against specific regions in the 16S RNA of *E. coli* small ribosomal subunit

| No. | Target on 16S rRNA | Sequences (5' to 3') | |
|---|---|---|---|
| 1 | Positions 520 to 503 | TGGCACGGAGTTAGCCGG | (SEQ ID NO: 1) |
| 2 | Positions 545 to 531 | GCACCCTCCGTATTA | (SEQ ID NO: 2) |
| 3 | Positions 523 to 503 | TGCTGGCACGGAGTTAGCCGG | (SEQ ID NO: 3) |
| 4 | Positions 526 to 503 | GGCTGCTGGCACGGAGTTAGCCGG | (SEQ ID NO: 4) |

TABLE 1-continued

List of antisense DNA oligomers targeted against specific regions in the 16S RNA of E. coli small ribosomal subunit

| Target on No. 16S rRNA | Sequences (5' to 3') | |
|---|---|---|
| 5 Positions 545 to 529 | GCACCCTCCGTATTACC | (SEQ ID NO: 5) |
| 6 Positions 528 to 517 | GCGGCTGCTGGC | (SEQ ID NO: 6) |
| 7 Positions 529 to 518 | CGCGGCTGCTGG | (SEQ ID NO: 7) |
| 8 Positions 925 to 913 | CGTCAATTCATTT | (SEQ ID NO: 8) |

Table 2 summarizes the results obtained with these agents, which demonstrate that some of these agents can modulate translational accuracy.

TABLE 2

Effect of antisense DNA oligomers on misreading in a poly(U)-directed translation system

| Conditions of translation | Misincorporation of leucine (in cpm) | |
|---|---|---|
| Without oligomer | 47 112 | |
| With oligomer N° 1 | 46 138 | (SEQ ID NO: 1) |
| With oligomer N° 2 | 46 508 | (SEQ ID NO: 2) |
| With oligomer N° 3 | 31 163* | (SEQ ID NO: 3) |
| With oligomer N° 4 | 30 349* | (SEQ ID NO: 4) |
| With oligomer N° 5 | 34 256* | (SEQ ID NO: 5) |
| With oligomer N° 6 | 65 316* | (SEQ ID NO: 6) |
| With oligomer N° 7 | 64 802* | (SEQ ID NO: 7) |
| With oligomer N° 8 | 45 012 | (SEQ ID NO: 8) |

Misreading in translation is assessed by measuring the misincorporation of leucine in a poly(U)-directed system, as described in the text. Results are the means of four to five independent experiments. Experimental variation is ±10%. The incorporation of the cognate aminoacid phenylalanine (500 814 ±5000 cpm) was not affected by the addition of the oligomers.

* indicates oligomers which affect translation accuracy of the ribosomes.

The second part of the present invention investigates specifically which agents decrease ribosomal frameshifting when ribosomes have to translate a shifty region corresponding to that present in HIV mRNA.

2. Effects of antisense DNA oligomers on frameshifting efficiency

An expression vector, pCAT-HIV(-1), encoding the chloramphenicol acetyltransferase (CAT) gene under control of a T7 promoter was derived from pLRC-CAT, an expression vector containing the CAT gene (see below). The CAT gene was modified by an extension encompassing the HIV frameshifting region, in the beginning of the coding region. Expression from pCAT-HIV(-1) leads to an active CAT protein, only when ribosomes change the translational reading frame, shifting by to the left, in the HIV shifting region. We have assessed the expression of the CAT gene from pCAT-HIV(-1) in vitro, in the presence or absence of antisense DNA oligomers, as follows: the CAT gene was first transcribed in vitro with T7 RNA polymerase and subsequently, the CAT messenger was translated with or without the DNA oligomers and the CAT activity was measured.

DNA oligomers which decrease CAT activity when using pCAT-HIV(-1), but do not affect CAT activity with control pLRC-CAT, are potential therapeutic agents against HIV. For comparison, an expression vector, pCAT-HIV(0) was also constructed, which contains the HIV frameshifting region in the beginning of the CAT gene, except that in this case, no frameshift was required to yield CAT enzyme.

Methods

1. Construction of CAT expression vectors containing an N-terminally modified CAT gene The CAT expression vector, pLR-CAT was constructed by excising from pACYC184 (New England Biolabs), the TagI—TagI fragment, which encodes the CAT coding sequence plus flanking regions, and ligating this fragment into the polylinker site of plasmid pBluescript SK⁻ (Stratagene), linearized with ClaI. A SphI site was created by site-directed mutagenesis around the initiation AUG triplet (AAATGG was substituted with GCATGC), resulting in pLRC-CAT. All manipulations were performed using protocols basically described by Sambrook et al. (Sambrook, J., Fritsch, E. F. and Maniatis, T. (1989) In Molecular Cloning. A Laboratory Manual, $2^d$ Ed., Cold Spring Harbor Laboratory, Cold Spring Harbor, N.Y.).

Figure 2A:
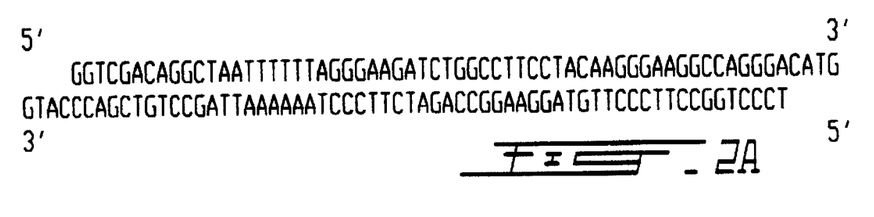
FIG. 2A illustrates the region encompassing the HIV-1 frameshifting element inserted in pCAT-HIV(−1), SEQ ID NO:10
Figure 2B:
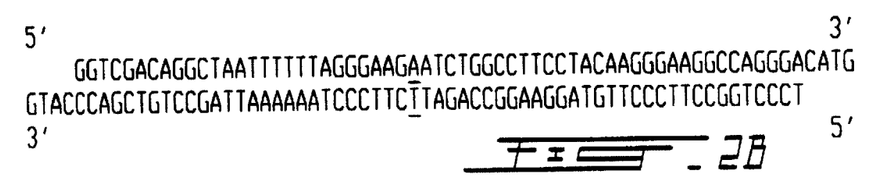
FIG. 2B illustrates the region encompassing the HIV-1 frameshifting element inserted in pCAT-HIV(0), SEQ ID NO: 11.

To construct pCAT-HIV(-1) and pCAT-HIV(0), synthetic double-stranded DNA containing the frameshifting region of HIV and sticky overhanging SphI ends was prepared and inserted into pLRC-CAT restricted with SphI. FIG. 2 gives the sequences of these fragments. The procedure was inspired from Vickers and Ecker (Vickers, T. A. and Ecker, D. J. (1992) Nucleic Acids Research, 20, 3945-3953).

2. 'In vitro' transcription and translation

In vitro transcription of pCAT-HIV(-1), pCAT-HIV(0) and pLRC-CAT linearized with Hind III was performed with T7 RNA polymerase, in a transcription mixture (100 µl) containing: 10 µg of linearized plasmid, 80 mM Hepes-KOH, pH 7.5, 12 mM $MgCl_2$, 2 mM spermidine, 5 mM dithiothreitol, 1000 units/ml of RNasin, 5 units/ml of pyrophosphatase, an optimal amount of T7 RNA polymerase, 500 µM ATP, CTP, UTP, 50 µM GTP and 500 µM of the cap analog $Me^7GpppG$ (Pharmacia). After incubation for 120 min. at 37° C., the transcripts were extracted with phenol-chloroform and ethanol-precipitated.

The RNA transcripts were translated for 1 h at 30° C. in a nuclease treated-reticulocyte lysate (Promega), following the instructions of the manufacturer. To analyze the size of the translation products, translation was performed in the presence of [$^{35}$S] methionine and the translation products analyzed by a 15% SDS/polyacrylamide gel electrophoresis. Unlabeled methionine was present when assessing the CAT activity.

Antisense DNA oligomers (1.5 µg), when present were added to the translation mixture (25 µl), prior to the addition of about 0.25 µg of RNA transcripts.

CAT assays

For CAT assays, following the Technical Bulletin TB084 of Promega, 25 µl of the translation mixture was mixed with 5 µl of butyryl CoA (at 5 mg/ml), 10 µl of [$^3$H] chloramphenicol (at 0.5 mM), 0.25 µCi, and 85 µl of a Tris-HCl buffer 0.25M (at pH 8). The mixture was incubated about 3 hours and CAT activity was quantitated by liquid scintillation counting of modified chloramphenicol, after xylene extraction.

Results

There is a very high degree of conservation in the ribosomal RNA from all living organisms (Raue, H. A. et al. (1988) Prog. Biophys. Molec. Biol., 51, 77-129; Gutell, R. R. (1993) Nucleic Acids Research, 21, 3051-3057; Neefs, J. M. et al. (1993) Nucleic Acids Research, 21, 3025-3049). In accordance with the first part of the present invention, the regions of *E. coli* 16S ribosomal RNA which are potential targets for oligomers which could affect translational accuracy, were identified. Because of the high conservation of ribosomal RNA, the corresponding regions in the 16S-like mammalian ribosomal RNA (18S rRNA), were immediately identified. Antisense oligomers were directed against these regions in order to affect ribosomal frameshifting. Table 3 presents some antisense DNA oligomers that have been used in accordance with the present invention.

TABLE 3

List of antisense DNA oligomers targeted against specific regions in the 18S RNA of the rabbit and human small ribosomal subunit

| No. | Target Positions on 18S rRNA | Sequences | |
|---|---|---|---|
| 6 | 603 to 614 in rabbits<br>613 to 624 in humans<br>(517 to 528) | GCGGCTGCTGGC | (SEQ ID NO: 6) |
| 7 | 604 to 615 in rabbits<br>614 to 625 in humans<br>(518 to 529) | CGCGGCTGCTG | (SEQ ID NO: 7) |
| 9 | 1190 to 1202 in rabbits<br>1195 to 1207 in humans<br>(913 to 925) | CGTCAATTCCTTT | (SEQ ID NO: 9) |

Numbers in brackets indicate the corresponding positions in *E. coli* 16S rRNA.

The complete sequence of 18S rRNA from rabbits and humans was obtained from EMBL nucleotide sequence library (Rairkar, A. et al. (1988) *Nucleic Acids Research*, 16, 3113; and Gonzalez, I. L. and Schmickel R. D. (1986) *Am. J. Hum. Genet.*, 38, 419–427, respectively). Table 4 presents the results obtained when translating the messengers corresponding to pCAT-HIV(−1), pCAT-HIV(0) and pLRC-CAT with rabbit ribosomes in the presence of a series of antisense DNA oligomers.

TABLE 4

Effect of antisense DNA oligomers on frameshifting with transcripts from pCAT-HIV(-1)

| Conditions of translation | CAT activity (in cpm) |
|---|---|
| Without oligomer | 2011 (100%) |
| With oligomer N° 6 | 430 (21 ± 5%) (SEQ ID NO: 6) |
| With oligomer N° 7 | 769 (38 ± 10%) (SEQ ID NO: 7) |
| With oligomer N° 9 | 706 (35 ± 10%) (SEQ ID NO: 9) |

CAT activity when translating with messengers transcribed from pCAT-HIV(−1) requires a ribosomal frameshifting. Translation was performed in a rabbit reticulocyte lysate as described in the text. The amount of oligomers added was 1.5 μg. Experiments are the means of six independent assays. In these assays, CAT activity was assessed, as described in the text, after a 3 hour incubation of the translation mixture with chloramphenicol. CAT activity is expressed in cpm. The numbers between brackets indicate the percent of CAT activity±the standard deviation when translation was performed in the presence of oligomers, a value of 100% being ascribed to the CAT activity in the absence of oligomers. The oligomers did not affect CAT activity measured with mRNA transcribed either from the control pLRC-CAT (67318±7000 cpm). When CAT activity was measured with mRNA transcribed from pCAT-HIV(0) (which contains an extension at the end of the coding region but does not require ribosomal frameshifting for CAT expression), its value was 59482±6000 cpm. It was decreased to about 85% of its initial value with oligomers 7 and 9, and to about 60% with oligomer 6.

Results in Table 4 clearly show that oligomers 6, 7 and 9 significantly decrease the frameshifting of ribosomes moving along the shifty region of HIV mRNA.

The therapeutic applications of oligonucleotides have been recently reviewed by Crooke et al. (Crooke, S. T. et al. (1992) *Annu. Rev. Toxicol.*, 32, 329–376). Cellular uptake of the oligomers will be enhanced by using liposomes (DOTMA, Gibco BRL or DOTAP, Boehringer Mannheim). A wide range of modifications has been described to enhance the intracellular stability of the oligomers. Among the various analogs which have been described, preferred modifications of the phosphodiester bonds generating methylphosphonates or modifications of the 2' position of the sugar (such as 2'-O-methyl oligomers) because they do not elicit a RNAse H activity and therefore will not damage the ribosomes.

The present invention will be more readily understood by referring to the following example which is given to illustrate the invention rather than to limit its scope.

EXAMPLE I

Effects of antisense DNA oligomers on the frameshifting of ribosomes in cultured human cells and on the replication of HIV-1 in HeLa-T4 cells An expression vector containing the CAT gene under control of an inducible promoter (pGRE5-CAT-HIV(−1)) was used in cultured human cells in order to assess the effects of antisense DNA oligomers on the frameshifting of the ribosomes. The CAT gene was modified, exactly as in the in vitro translation assays, by an extension encompassing the HIV frameshifting region in the beginning of the coding region. For comparison, a control expression vector, pGRE5-CAT-HIV(0), was also constructed, which contains the HIV frameshifting region in the beginning of the CAT gene, except that no frameshift is required with this construction to produce CAT enzyme.

The inhibitory effect of the DNA oligomers on the replication of HIV-1 was assessed by measuring HIV reverse transcriptase activity in the cell-free supernatant of cultured cells infected with HIV.

The DNA oligomers used in the assays with the cultured cells were modified so as to avoid degradation by intracellular nucleases and also to avoid that they trigger a RNAse H activity, which would attack their target RNA molecules. Modifications involved either the phosphodiester bond (methylphosphonates) or the 2' position of the sugar of the oligomers (2'-O-methyl phosphodiesters) (Crooke, S. T. et al. (1992) *Annu. Rev. Toxicol.*, 32, 329–376).

Synthesis of methylphosphonates and 2'-O-methyl oligomers

All oligodeoxynucleotide syntheses were performed with an automated DNA synthesizer (Millipore Expedite Nucleic Acid Synthesis System Model 8909™). The methylphosphonates were synthesized and deprotected following the procedure outlined by Hogrefe R. I. et al. ((1993) *Nucleic Acids Research*, 21, 2031–2038) and the 2'-O-methyl phosphodiesters were synthesized and deprotected following the standard protocol supplied by the manufacturer for oligoribonucleotides. The DNA oligomers were purified on C18 SepPak™ cartridges (Waters).

Expression vectors

The expression vectors were derivatives of the EBV episomal vector p220.2-pGRE 5/CAT plasmid constructed by Mader, S. and White, J. H. ((1993) *Proc. Natl. Acad. Sci.*

Figure 3A:
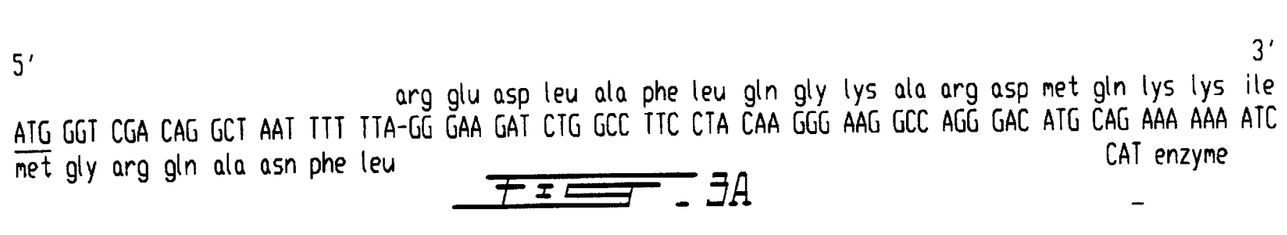
FIG. 3A illustrates the beginning of the CAT coding region in pCAT-HIV(−1), SEQ ID NO:12 and the corresponding amino acid sequence of the reporter protein, upper sequence, SEQ ID NO:15; lower sequence SEQ ID NO:13.
Figure 3B:
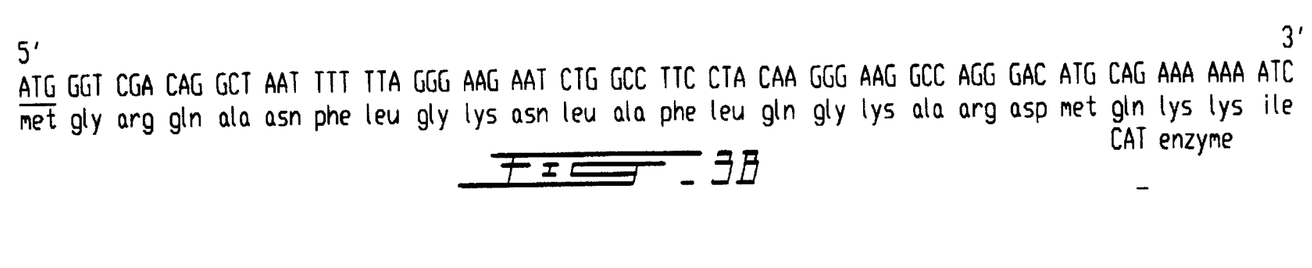
FIG. 3B illustrates the beginning of the CAT coding region in pCAT-HIV(0), SEQ ID NO:16 and the corresponding amino acid sequence of the reporter protein, SEQ ID NO:17.

USA, 90, 5603–5607), which contains the CAT gene under control of a synthetic promoter GRE5, which is inducible with dexamethasone. The derivatives which we constructed are pGRE5-CAT-HIV(−1) and pGRE5-CAT-HIV(0) which contain a N-terminally modified CAT gene by insertion of the frameshifting region of HIV genome, exactly as described in FIGS. 3A and 3B, respectively. CAT expression requires a ribosome frameshifting with pGRE5-CAT-HIV(−1), but not with pGRE5-CAT-HIV(0).

Plasmid pSv-βGal (Promega), an expression vector which codes for β-galactosidase activity, was used to normalize transfection efficiencies.

Cell cultures

The cell line used for measuring the frameshift of ribosomes is a HeLa cell line, a human epitheloid carcinoma cell line deposited at the American Type Culture Collection (12301 Parklawn Drive, Rockville, Md. 20852 USA) under deposit number ATCC CCL2. The cells were cultivated in Dulbecco's modified Eagle's medium supplemented with 10% fetal bovine serum, 100 U/ml penicillin G and 100 μg/ml streptomycin. Transfection with the eukaryotic expression vector was carried out by the standard calcium phosphate coprecipitation technique for 4 h followed by a glycerol shock. Cells at 50% confluency in 10-cm plates were transfected with 20 μg of pGRE5-CAT-HIV(−1) or pGRE5-CAT-HIV(0), 10 μg of pSV-βgal and with or without DNA oligomers (about 40 μg). Dexamethasone (Sigma) was added at 25 nM immediately after transfection and 24 h after transfection. Cells were harvested about 48 h after transfection.

The cell line used for measuring the replication of HIV was the HeLa-T4 (HT-6C) cell line, which was obtained through the AIDS Research Reference Reagent Program, Division of AIDS, NIAID, NIH (Chesebro, B. and Wehrly, K. (1988) *J. Virol.* 62, 3779–3788).

Effect of the oligomers on the frameshifting of the ribosomes

Cells were harvested in 100 μl of 0.25 M Tris-HCl (pH 8); 80 μl were assayed for CAT activity by liquid scintillation counting using the same procedure as in in vitro translation assays, as described in the Technical Bulletin #084 from Promega, whereas 20 μl was used for assaying the β-galactosidase activity, with a colorimetric assay in which o-nitrophenyl β-D-galacto-side (ONPG) is cleaved to produce o-nitrophenol, as described in a standard protocol (Miller J. H. (1972) *Experiments in Molecular Genetics*, Cold Spring Harbor Laboratory Press, New-York, pp 352–355).

Effect of the oligomers on the replication of HIV-1 virus

HeLa-T4 cells ($1 \times 10^6$) were seeded into 10 cm plates in 8 ml of Dulbecco's modified Eagle's medium supplemented with 10% fetal bovine serum 24 h before transfection. HeLa-T4 cells were transfected with 15 μg of HIV-1 provirus (HXBH10) DNA (Terwilliger, E. F. et al. (1989) *Proc. Natl. Acad. Sci. USA*, 86, 5163–5167) and 20 μg of oligomers by the standard calcium phosphate method; 12 h after the transfection, the cells were washed and cultured in 8 ml of Dulbecco's modified Eagle's medium supplemented with 10% fetal bovine serum; 48 h after the transfection, the supernatants were collected for HIV-1 reverse transcriptase activity assay: 50 μl of cell-free supernatants were clarified by low-speed centrifugation (3000 rpm for 20 min) and assayed as described (Lee, M. H. et al. (1987) *J. Clin. Microbiol.*, 25, 1717–1721).

The results on the effect of the oligomers on the frameshifting of ribosomes are presented in Table 5. These results clearly indicate that the modified oligomers decrease the ribosomal frameshifting and therefore have the capacity to interfere with HIV development.

TABLE 5

Effect of modified DNA oligomers on the frameshifting of ribosomes in cultured HeLa cells

| Conditions of translation | CAT activity |
|---|---|
| Without oligomer | 100% |
| With oligomer 6-3 mp* | 49 ± 5% (SEQ ID NO: 6) |
| With oligomer 6-8 om* | 35 ± 5% (SEQ ID NO: 6) |
| With oligomer 7-8 om* | 40 ± 5% (SEQ ID NO: 7) |

Oligomer 6-3 mp* is a chimeric methylphosphonate derivative of oligomer 6 (see Table 3) with 3 modifications: GCmGGCTGmCTGGmC (SEQ ID NO:6) (the letter m refers to the internucleotide linkages where the phosphodiester is substituted with a methylphosphonate linkage).

Oligomer 6-8 om* and 7-8 om* are 2'-O-methyl derivatives of oligomers 6 and 7 (Table 3) with 8 modifications: $GC^{Ome}G^{Ome}G^{Ome}C^{Ome}TG^{Ome}C^{Ome}TG^{Ome}G^{Ome}C$ (SEQ ID NO:6) and $CG^{Ome}C^{Ome}G^{Ome}G^{Ome}C^{Ome}TG^{Ome}C^{Ome}TG^{Ome}G$ (SEQ ID NO:7) where the superscript Ome is 2'-O-methyl, indicating that the nucleotide contains a ribose with a 2'-O-methyl group.

The CAT activity is expressed as the mean±the standard deviation of three independent transient expression experiments with pGRE5-CAT-HIV(−1) where CAT expression requires ribosome frameshifting. The values for CAT activity (about 6000 cpm for 100%) have been normalized relative to β-galactosidase expression.

The oligomers did not affect CAT activity with pGRE5-CAT-HIV(0), indicating that they do not affect the normal function of the ribosomes.

Figure 4:
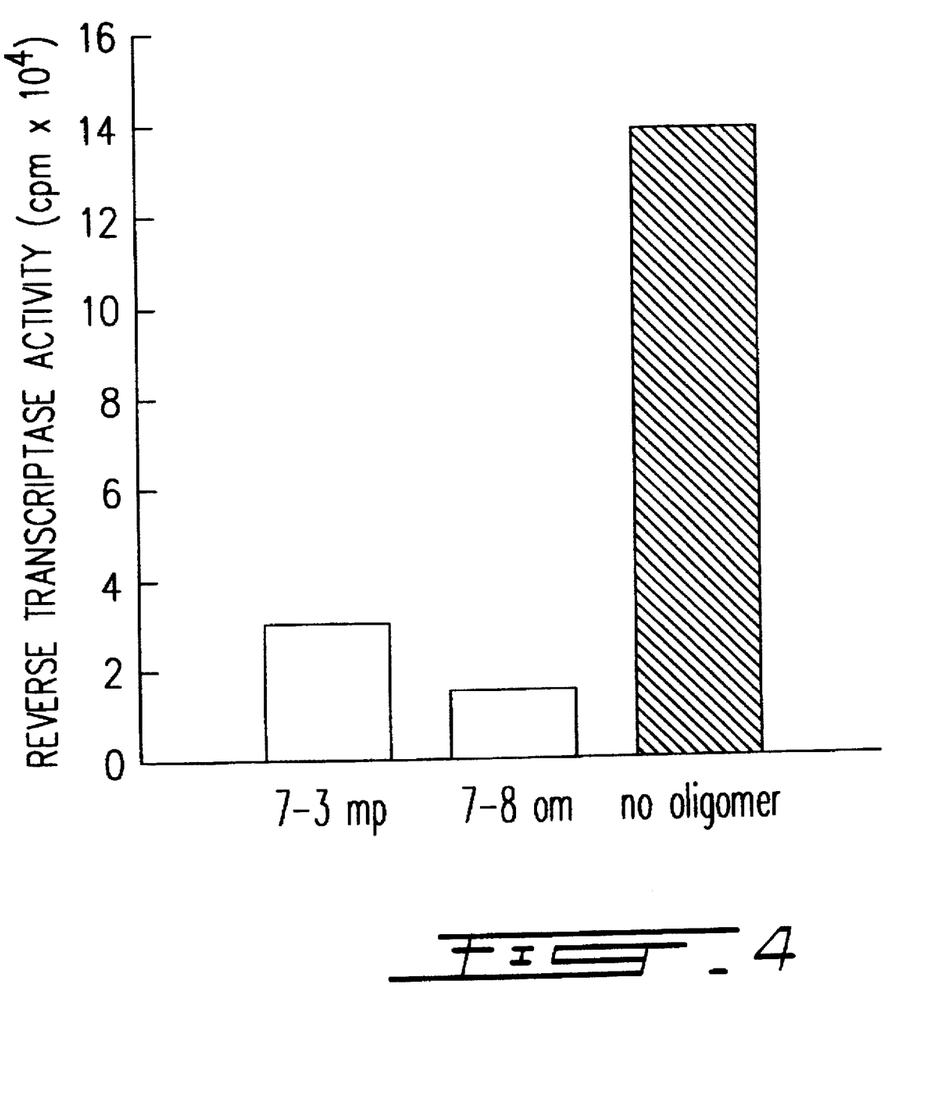
FIG. 4 is a graph of the effect of the oligomers on HIV reverse transcriptase activity in supernatants of cultured cells infected with HIV.

FIG. 4 illustrates an example of the effect of the oligomers on HIV-1 replication, as assessed by measuring HIV reverse transcriptase activity in supernatants of cultured cells infected with HIV. The severe decrease in HIV reverse transcriptase activity demonstrates that the oligomers efficiently interfere with viral replication.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. An antisense DNA oligomer which is complementary to the region of the human 18 S rRNA consisting of nucleotides 595 to 641, wherein said oligomer decreases the occurrence of ribosomal frameshifting and inhibits the expression of HIV enzymatic proteins.

2. The antisense DNA oligomer of claim 1 having a sequence selected from the group consisting of SEQ ID NO:3, SEQ D NO:4, SEQ ID NO:5, SEQ ID NO:6, and SEQ ID NO:7.

3. An antisense oligomer having the sequence of SEQ ID NO:9.

4. A composition which inhibits HIV in cell culture comprising an antisense DNA oligomer of claim 1 and a pharmaceutically acceptable carrier.

5. A method of inhibiting HIV in cell culture comprising administering the composition of claim 4.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:1:

TGGCACGGAG TTAGCCGG  18

( 2 ) INFORMATION FOR SEQ ID NO:2:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:2:

GCACCCTCCG TATTA  15

( 2 ) INFORMATION FOR SEQ ID NO:3:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:3:

TGCTGGCACG GAGTTAGCCG G  21

( 2 ) INFORMATION FOR SEQ ID NO:4:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:4:

GGCTGCTGGC ACGGAGTTAG CCGG                                                              24

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: YES     ( x i ) SEQUENCE DESCRIPTION: SEQ ID NO:5:

GCACCCTCCG TATTACC                                                                      17

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: YES     ( x i ) SEQUENCE DESCRIPTION: SEQ ID NO:6:

GCGGCTGCTG GC                                                                           12

( 2 ) INFORMATION FOR SEQ ID NO:7:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: YES     ( x i ) SEQUENCE DESCRIPTION: SEQ ID NO:7:

CGCGGCTGCT GG                                                                           12

( 2 ) INFORMATION FOR SEQ ID NO:8:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: YES     ( x i ) SEQUENCE DESCRIPTION: SEQ ID NO:8:

CGTCAATTCA TTT                                                                          13

( 2 ) INFORMATION FOR SEQ ID NO:9:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:9:

CGTCAATTCC TTT    13

( 2 ) INFORMATION FOR SEQ ID NO:10:

( i ) SEQUENCE CHARACTERISTICS:
    ( A ) LENGTH: 62 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc ="Containing sticky
        overhanging Sph 1 ends"

( i i i ) HYPOTHETICAL: NO ( i v ) ANTI-SENSE: NO ( x i ) SEQUENCE DESCRIPTION: SEQ ID NO:10:

GGTCGACAGG CTAATTTTTT AGGGAAGATC TGGCCTTCCT ACAAGGGAAG GCCAGGGACA    60

TG    62

( 2 ) INFORMATION FOR SEQ ID NO:11:

( i ) SEQUENCE CHARACTERISTICS:
    ( A ) LENGTH: 63 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc ="Containing sticky
        overhanging Sph 1 ends"

( i i i ) HYPOTHETICAL: NO ( i v ) ANTI-SENSE: NO ( x i ) SEQUENCE DESCRIPTION: SEQ ID NO:11:

GGTCGACAGG CTAATTTTTT AGGGAAGAAT CTGGCCTTCC TACAAGGGAA GGCCAGGGAC    60

ATG    63

( 2 ) INFORMATION FOR SEQ ID NO:12:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: NO ( i v ) ANTI-SENSE: NO ( i x ) FEATURE:

( A ) NAME/KEY: CDS
                    ( B ) LOCATION: 1..24

( i x ) FEATURE:
                    ( A ) NAME/KEY: CDS
                    ( B ) LOCATION: 24..77

( x i ) SEQUENCE DESCRIPTION: SEQ ID NO:12:

```
ATG GGT CGA CAG GCT AAT TTT TTA GGGAAGATCT GGCCTTCCTA CAAGGGAAGG      54
Met Gly Arg Gln Ala Asn Phe Leu
 1               5

CCAGGGACAT GCAGAAAAAA ATC                                             77
```

( 2 ) INFORMATION FOR SEQ ID NO:13:

( i ) SEQUENCE CHARACTERISTICS:
                    ( A ) LENGTH: 8 amino acids
                    ( B ) TYPE: amino acid
                    ( D ) TOPOLOGY: linear ( i i ) MOLECULE TYPE: protein ( x i ) SEQUENCE DESCRIPTION: SEQ ID NO:13:

```
Met Gly Arg Gln Ala Asn Phe Leu
 1               5
```

( 2 ) INFORMATION FOR SEQ ID NO:14:

( i ) SEQUENCE CHARACTERISTICS:
                    ( A ) LENGTH: 77 base pairs
                    ( B ) TYPE: nucleic acid
                    ( C ) STRANDEDNESS: single
                    ( D ) TOPOLOGY: linear ( i i ) MOLECULE TYPE: other nucleic acid ( i i i ) HYPOTHETICAL: NO ( i v ) ANTI-SENSE: NO ( i x ) FEATURE:
                    ( A ) NAME/KEY: CDS
                    ( B ) LOCATION: 24..77

( x i ) SEQUENCE DESCRIPTION: SEQ ID NO:14:

```
ATGGGTCGAC AGGCTAATTT TTT AGG GAA GAT CTG GCC TTC CTA CAA GGG         50
                        Arg Glu Asp Leu Ala Phe Leu Gln Gly
                         10                      15

AAG GCC AGG GAC ATG CAG AAA AAA ATC                                   77
Lys Ala Arg Asp Met Gln Lys Lys Ile
 20                  25
```

( 2 ) INFORMATION FOR SEQ ID NO:15:

( i ) SEQUENCE CHARACTERISTICS:
                    ( A ) LENGTH: 18 amino acids
                    ( B ) TYPE: amino acid
                    ( D ) TOPOLOGY: linear ( i i ) MOLECULE TYPE: protein ( x i ) SEQUENCE DESCRIPTION: SEQ ID NO:15:

```
Arg Glu Asp Leu Ala Phe Leu Gln Gly Lys Ala Arg Asp Met Gln Lys
 1               5                  10                  15

Lys Ile
```

( 2 ) INFORMATION FOR SEQ ID NO:16:

( i ) SEQUENCE CHARACTERISTICS:

(A) LENGTH: 78 base pairs
(B) TYPE: nucleic acid
(C) STRANDEDNESS: single
(D) TOPOLOGY: linear (ii) MOLECULE TYPE: other nucleic acid (iii) HYPOTHETICAL: NO (iv) ANTI-SENSE: NO (ix) FEATURE:
    (A) NAME/KEY: CDS
    (B) LOCATION: 1..78

(xi) SEQUENCE DESCRIPTION: SEQ ID NO:16:

| ATG | GGT | CGA | CAG | GCT | AAT | TTT | TTA | GGG | AAG | AAT | CTG | GCC | TTC | CTA | CAA | 48 |
| Met | Gly | Arg | Gln | Ala | Asn | Phe | Leu | Gly | Lys | Asn | Leu | Ala | Phe | Leu | Gln | |
| 1 | | | | | 5 | | | | | 10 | | | | | | |

| GGG | AAG | GCC | AGG | GAC | ATG | CAG | AAA | AAA | ATC | | | | | | | 78 |
| Gly | Lys | Ala | Arg | Asp | Met | Gln | Lys | Lys | Ile | | | | | | | |
| 15 | | | | | 20 | | | | | 25 | | | | | | |

(2) INFORMATION FOR SEQ ID NO:17:

(i) SEQUENCE CHARACTERISTICS:
    (A) LENGTH: 26 amino acids
    (B) TYPE: amino acid
    (D) TOPOLOGY: linear (ii) MOLECULE TYPE: protein (xi) SEQUENCE DESCRIPTION: SEQ ID NO:17:

| Met | Gly | Arg | Gln | Ala | Asn | Phe | Leu | Gly | Lys | Asn | Leu | Ala | Phe | Leu | Gln |
| 1 | | | | 5 | | | | | 10 | | | | | 15 | |

| Gly | Lys | Ala | Arg | Asp | Met | Gln | Lys | Lys | Ile |
| | | | 20 | | | | | 25 | |